Figure 1:
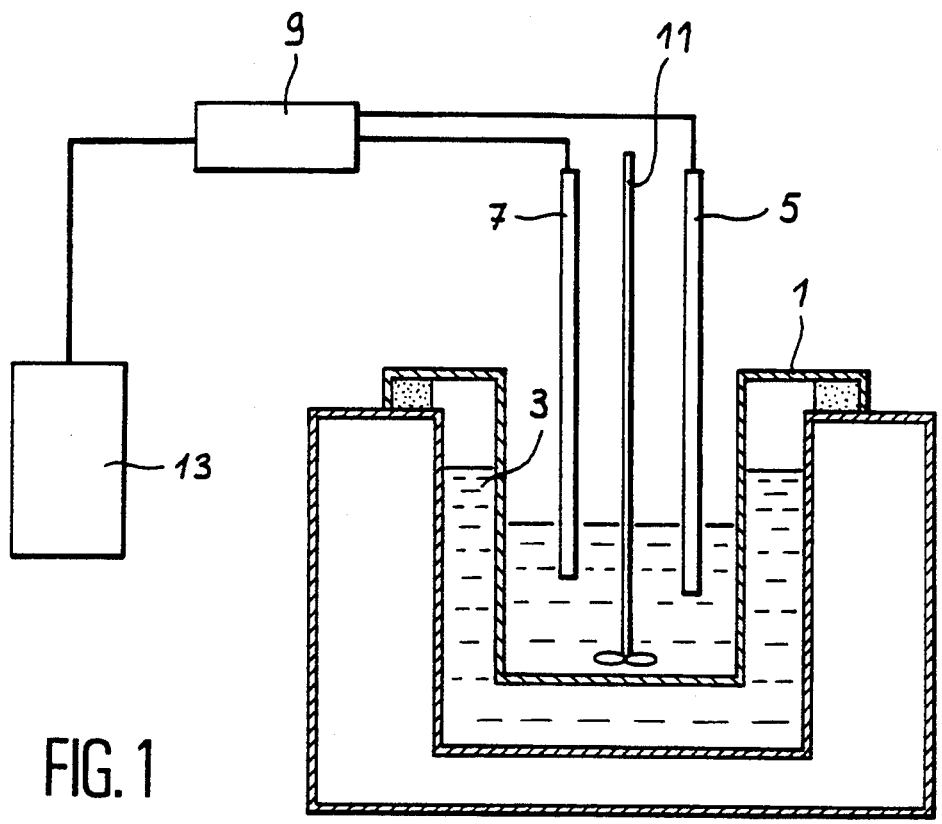

US005376243A

United States Patent [19]
Lecouteux et al.

[11] Patent Number: 5,376,243
[45] Date of Patent: Dec. 27, 1994

[54] PROCESS FOR THE DETERMINATION OF IODINE IN LOW CONCENTRATION IN A NITRATE SOLUTION, PARTICULARLY A URANYL NITRATE SOLUTION

[75] Inventors: Claude Lecouteux, Avignon; Jean-Yves Doyen, Saint André de Roquepertuis, both of France

[73] Assignee: Commissariat a l'Energie Atomique, Paris, France

[21] Appl. No.: 93,691

[22] Filed: Jul. 20, 1993

[30] Foreign Application Priority Data

Jul. 21, 1992 [FR] France .................. 92 08984

[51] Int. Cl.$^5$ .......................... G01N 27/333
[52] U.S. Cl. .................. 204/153.13; 204/416; 204/419
[58] Field of Search ............ 204/153.1, 153.13, 416, 204/418, 419

[56] References Cited

U.S. PATENT DOCUMENTS

| 3,314,864 | 4/1967 | Hersch | 204/431 |
| 3,380,905 | 4/1968 | Clark | 204/415 |
| 3,923,608 | 12/1975 | Frant et al. | 204/419 |
| 4,172,778 | 10/1979 | Van de Leest, et al. | 204/419 |

OTHER PUBLICATIONS

Orion Research Analytical Methods Guide, 2nd. ed., Jan. 1972, p. 4.

Primary Examiner—T. Tung
Attorney, Agent, or Firm—Oblon, Spivak, McClelland, Maier & Neustadt

[57] ABSTRACT

The invention relates to a process for the determination of iodine in low concentration in a nitrate solution, particularly a uranyl nitrate solution.

According to this process, to the sample to be determined is added a reducing agent such as ascorbic acid in order to maintain the iodine in the iodide state, followed by the measurement of the potential difference $E_1$ between a selective iodide ion electrode (5) and a reference electrode (7), after which there is a successive addition of a first and a second iodide solution having known iodide concentrations and containing a reducing agent, accompanied by the measurement after each addition of the potential differences $E_2$ and then $E_3$ between the electrodes (5) and (7), followed by the calculation from $E_1$, $E_2$ and $E_3$, the concentrations and volumes of the additions, the initial iodine concentration of the solution.

13 Claims, 2 Drawing Sheets

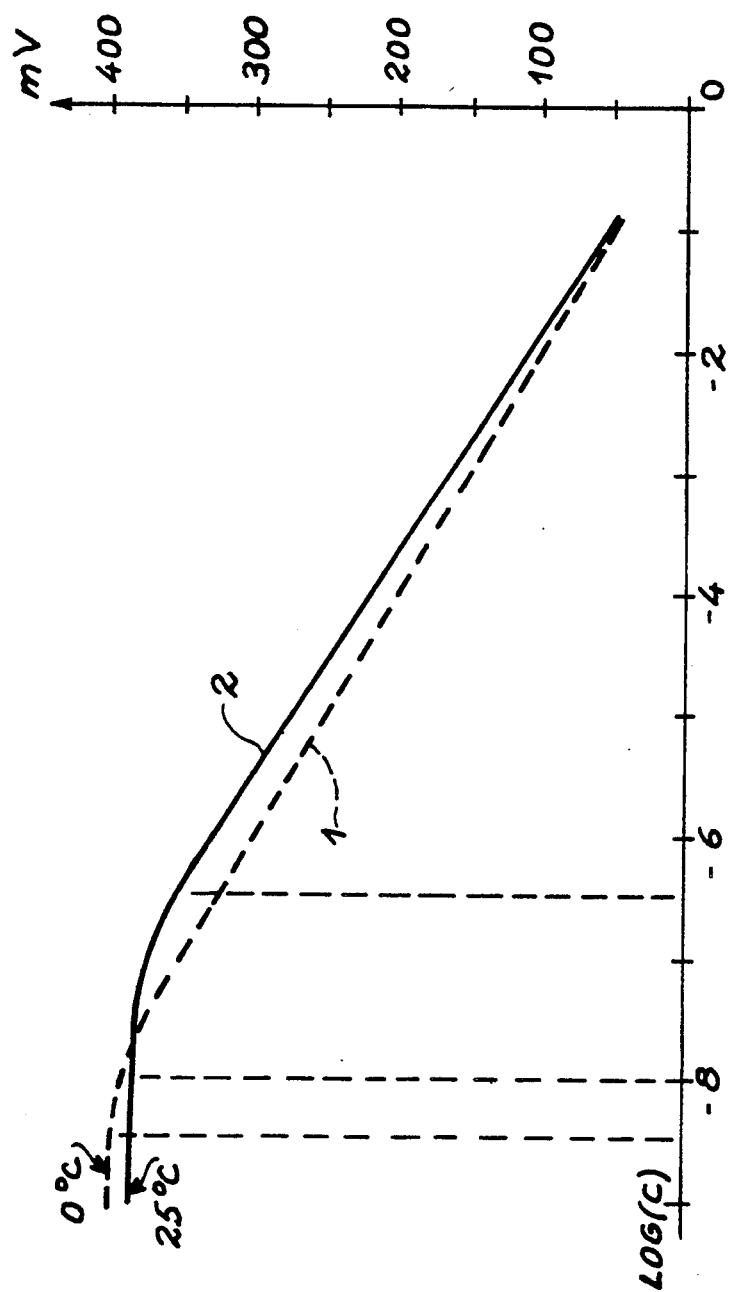

PROCESS FOR THE DETERMINATION OF IODINE IN LOW CONCENTRATION IN A NITRATE SOLUTION, PARTICULARLY A URANYL NITRATE SOLUTION

DESCRIPTION

The invention relates to a process for the determination of iodine in low concentration in an aqueous solution containing an oxidizing agent. More specifically, it relates to the determination of iodine in uranyl nitrate solutions from the reprocessing of irradiated nuclear fuels.

In irradiated nuclear fuel reprocessing installations, the standard practice is to dissolve the fuel in a hot concentrated nitric acid solution. During said dissolving operation, most of the iodine contained in the fuel is entrained in the vapour phase with the steam and the nitrogen oxides, but a small part of the iodine is present in the dissolving solution.

However, as from a certain concentration threshold, the presence of iodine in these dissolving solutions is prejudicial, because it disturbs the following extraction cycles used for separating the uranium, plutonium and fission products.

It is therefore important to be able to accurately determine the iodine quantity present in these dissolving solutions, which can contain up to 250 g/l of uranium VI.

The determination process used must be fast, but in particular very sensitive, because the iodine concentrations of these solutions are generally very low, e.g. approximately $10^{-8}$ to $10^{-9}$ mole/liter of iodine. Therefore, the chemical determination processes cannot be used, because they have an inadequate accuracy.

Use has also been made of electrochemical determination methods for this purpose, e.g. potentiometry, but unfortunately it is only possible at present to determine iodine up to $10^{-7}$ mole/liter.

Moreover, the use of this method implies that all the iodine is present in the solution in iodide form. However, in the presence of oxidizing nitrate, the iodide is retransformed into iodine and the solution evolves in time.

The dissolving solution also contains numerous ions, e.g. U, Pu, Am, Cm, Rb, Sr, U, Zr, Nb, No, Tc, Ru, Rh, Pd, Ag, Cd, In, Sn, Sb, Fe and the presence of these ions complicates the determination, because a certain number of them may interfere with the determination or the reagents used.

The present invention relates to a process for the determination of iodine in low concentration, e.g. 1 to $5 \cdot 10^{-8}$ mole/liter, in an aqueous solution, which makes it possible to obtain a good sensitivity, even in the presence of numerous parasitic ions, and more particularly applies to uranyl nitrate solutions, even when they contain salts.

The invention therefore relates to a process for the determination of iodine in low concentration in aqueous solution containing an oxidizing nitrate, characterized in that it comprises the following successive stages:

1°) adding to a sample of the solution to be determined a reducing agent in order to reduce all the iodine contained therein into iodide and obtain a sample of volume $V_0$ having an iodide concentration $C_0$, 2°) measuring the potential difference $E_1$ between a selective iodide ion electrode and a reference electrode, both immersed in the sample of volume $V_0$, 3°) carrying out a first addition of iodide to the sample by adding to it an iodide solution volume $V_1$ containing the same reducing agent and having a known iodide concentration $C_1$, 4°) measuring the potential difference $E_2$ between the selective electrode and the reference electrode after the first iodide addition to the sample, 5°) carrying out a second iodide addition to the sample by adding to it an iodide solution volume $V_2$ containing the same reducing agent and having a known iodide concentration $C_2$, 6°) measuring the potential difference $E_3$ between the selective electrode and the reference electrode following said second iodide addition to the sample and 7°) determining from $E_1$, $E_2$, $E_3$, $V_1$, $V_2$, $C_1$ and $C_2$ the iodide concentration $C_0$ of the reduced sample and the iodine concentration of the solution, stages 2 to 6 being performed at a temperature of 0° to 5° C.

Preferably, the reducing agent used is ascorbic acid.

In this process, the use of a reducing agent such as ascorbic acid for reducing the iodine into iodide is especially interesting, because it makes it possible to stabilize the iodine in the solution in the form of iodide and in this way obtain the desired determination sensitivity.

Moreover, the fact of performing stages 2°) to 6°) at a temperature of 0° to 5° C. obviates the prejudicial influence of a dissolving of I- ions obtained from the selective electrode in the sample, because said dissolving is greatly reduced at such temperatures.

The determination process according to the invention is based on the use of the NERNST relation, which links the potential difference E established between a selective iodide ion electrode and a reference electrode with the activity $A_x$ of the iodide ions of the solution or their concentration, said relation being written:

$$E = E_0 + RT/nF \log A_x$$

Thus, in the determination according to the invention, the value of $E_1$ is dependent on the initial iodide ion concentration $C_0$ and the values $E_2$ and $E_3$ are respectively dependent on the concentrations $C_1$ and $C_2$ and the volumes $V_1$ and $V_2$ of the iodide additions.

Moreover, by appropriately choosing the respective iodide concentrations $C_1$ and $C_2$ and the volumes $V_1$ and $V_2$ of the first and second additions, it is possible to get round the prejudicial influence of the other ions of the solution on the determination and accurately determine the initial iodine concentration $C_0$ of the sample.

According to the invention, the ascorbic acid quantity added to the sample must be adequate to reduce to iodide any iodine which it contains.

Generally use is made of an excess compared with the necessary iodine equivalent quantity. For example, it is possible to use 1 mole/liter ascorbic acid solutions and add 2 volumes of said solution to one volume of sample to obtain the reduced sample of volume $V_0$ having an iodine concentration $C_0$ equal to ⅓ of the initial iodine concentration of the solution to be determined.

In the process according to the invention, use is advantageously made for the iodide ion selective electrode of an electrode whose active surface is constituted by an AgI/AgS crystal. This electrode can be associated with a reference electrode constituted by a mercurous sulphate electrode.

With such a selective electrode, stages 2°) to 6°) are preferably performed at a temperature close to 0° C., because the dissolving of the ions of the AgI crystal of the selective electrode in the solution is very reduced at 0° C., the solubility constant of AgI decreasing with the temperature.

Thus, with the process according to the invention, it is possible to determine by means of a selective electrode the iodide ions, in a uranyl nitrate solution, at very low concentrations (approximately $5 \cdot 10^{-8}$M). In order to be able to carry out measurements in this concentration range, compared with conventional determination, it is necessary to significantly lower the iodide ion determination limit (conventionally exceeding $10^{-7}$M).

In order to achieve this objective two improvements have been made to the determination:
the measuring cell is kept at approximately 0° C. in a range between 0° and 5° C. throughout the determination;
an original iterative calculation makes it possible, by using the voltage values of the electrode following a first and then a second determined addition, to extrapolate the electrode response curve in its non-linear part and consequently obtain improvements with respect to the determination threshold.

Hereinafter, the advantages linked with the lowering of the temperature are described, whilst details are given of the iterative calculation which, by using the experimental values of the voltages of the electrode, makes it possible to lower the determination threshold.

The invention is described in greater detail hereinafter relative to non-limitative embodiments and with reference to the attached drawings, wherein show:

FIG. 1 A diagrammatic representation of a determination cell usable for performing the process according to the invention.

Figure 2:
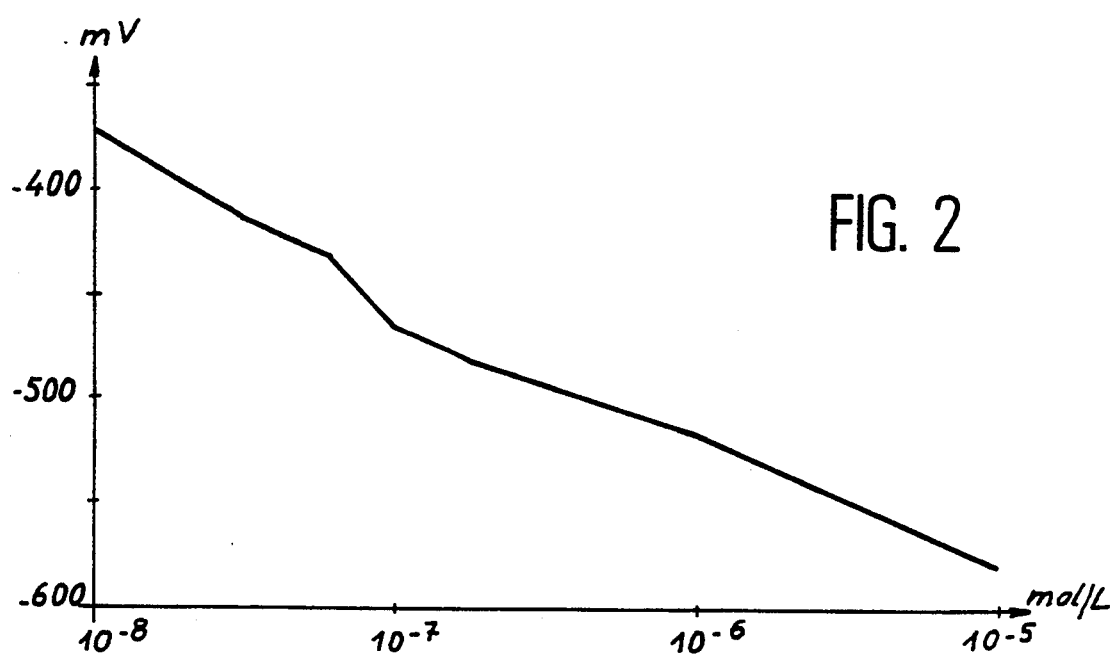

FIG. 2 A graph showing the evolution of the potential (in mV) measured in said cell as a function of the iodide content of the solution (in mole/l).

FIG. 3 A graph illustrating the evolution of the potential (in mV) as a function of the iodide concentration (in log C) at 0° C. and 25° C.

FIG. 1 shows that the determination cell comprises a container (1) for receiving the sample to be determined, said container being placed in a thermostatically controlled bath (3) so that the sample can be kept at the desired temperature. Within the container can be placed a first electrode (5) constituted by an iodide ion selective electrode and a second electrode (7) constituted by a reference electrode, said two electrodes being connected to a potentiometer (9) making it possible to measure the potential difference between the electrodes (5) and (7). A stirrer (11) is also placed in the container (1).

In said cell, it is possible to use as the selective electrode (5), an AgI/AgS electrode such as the ORLON type 94-53 electrode, whilst the reference electrode (7) can be constituted by a mercurous sulphate electrode, such as the TACUSSEL type S8 electrode. The stirrer (11) is advantageously a blade stirrer, because magnetic stirrers are unusable because they produce interference prejudicial to a correct measurement of the potential. The potentiometer (9) can be a METTLER type DL40 GP potentiometer.

Advantageously, the determination cell is completed by a data processing means (13) connected to the potentiometer (9) for processing the informations supplied by the potentiometer and the information concerning the volumes $V_1$ and $V_2$ and the iodide concentration $C_1$ and $C_2$ in order to obtain from said information the iodine concentration of the solution sample to be determined. This processing means can be a BULL MICRALL 30 computer equipped with a METTLER interface.

With a view to using said cell for the determination of iodine, the cell is calibrated beforehand by measuring the potential between the electrodes (5) and (7) for different iodine concentrations of the solution.

For this purpose, into the container (1) maintained at a temperature close to 5° C., are introduced 10 ml of a uranyl nitrate solution and 20 ml of a 0.75 mole/l ascorbic acid solution. The ascorbic acid solution was obtained by dissolving 132 g of ascorbic acid in ultrapure water in order to obtain a final volume of 1 liter.

The uranyl nitrate solution was obtained by dissolving 290 g of uranium oxide in 3N nitric acid and adjusting the free acidity by adding $H_2O$ or $HNO_3$ in concentrated form to obtain an acidity of 3N in the final 1 liter volume.

To the container (1) were then added iodide ions with the ascorbic acid in order to obtain iodide concentrations between $10^{-8}$ mole/l and $10^{-5}$ mole/l, the iodide solution volumes added being sufficiently small not to significantly modify the composition of the solution to be analyzed.

The iodide solutions used for obtaining these concentrations are prepared by diluting in the 0.75 mole/l ascorbic acid solution, a $10^{-8}$ mole/l potassium iodide mother solution obtained by dissolving 16.6 g of KI in ultrapure water to obtain a final volume of 100 ml in a final volume of 50 ml.

For example, on each occasion addition takes place of 50 μl of iodide solution containing ascorbic acid and following each addition determination takes place of the potential difference between the selective electrode (5) and the reference electrode (7).

The results obtained are given in FIG. 2, which shows the evolution of the potential (in mV) as a function of the decimal logarithm of the iodine concentration of the sample (in mole/l). It can be seen that the response is linear in the concentration range $10^{-5}$ to $10^{-7}$M, but as from $10^{-7}$M, the curve no longer respects the NERNST law. As from $10^{-9}$M the threshold due to the solubility of the crystal of the electrode is reached.

The calibration curve shown in FIG. 2 is only useful for evaluating the iodide ion quantities which have to be present in the two additions carried out during a determination according to the invention, as will be seen in the determination example given hereinafter. In said example, a description is given of a determination carried out according to the invention in the cell shown in FIG. 1.

For said determination introduction firstly takes place into the container (1) of 10 ml of solution sample to be analyzed and 20 ml of an aqueous 0.75 mole/l ascorbic acid solution. The thermostatically controlled bath (3) is put into operation in order to obtain a constant temperature close to 0° C. and then the assembly constituted by the electrodes (5) and (7) and the stirrer (11) is immersed in the solution. These electrodes were kept at 0° C. for half a day before starting the first determination.

Under these conditions, the potentiometer (9) indicates the potential difference between the electrodes (5) and (7).

When the stability criterion is observed, namely after a stabilization time such that the potential variation is below 0.07 mV/min, the value of the potential $E_1$ (in mV) is transferred to the data processing means (13).

This is followed by the first iodide addition by adding to the container (1) a volume $V_1$ of iodide solution containing ascorbic acid and having an iodide concentration $C_1$. The volume $V_1$ of said addition and its concentration $C_1$ are chosen according to the calibration curve of FIG. 2 in such a way that following said addition there is a potential $E_2$ such that $7 < E_2 - E_1 < 15$ mV. Moreover, the volume $V_1$ must be low, preferably at the most equal to $10^{-3} V_0$, e.g. between 10 and 50 µl.

To this end, addition takes place of 20 µl of a potassium iodide solution with 0.1 mole/l of iodide obtained from the iodide mother solution by diluting in the 0.75M ascorbic acid solution.

Following said first addition, the potential $E_2$ is determined and is also introduced into the data processing means (13) when the stability criterion is observed.

This is followed by the second addition of iodide solution containing ascorbic acid, which e.g. has an iodide concentration $C_2$ and a volume $V_2$ such that $C_2 V_2$ is equal to 5 times $C_1 V_1$. As for the first addition, $V_2$ must be low and not exceed $10^{-3} V_0$.

For example, addition takes place of 10 µl of a 1 mole/l potassium iodide solution also containing ascorbic acid and obtained as for the first addition.

After determination of the potential $E_3$ of the solution after the second addition, said information is transferred to the processing means (13), which calculates by iteration the initial concentration $C_0$ of the sample of volume $V_0$ from the following equations:

$$p = (E_3 - E_1)/\log|1 + (k+1)C/C_0| \qquad (1)$$

$$C_0 = C/|10^{(E_2-E_1)/p} - 1| \qquad (2)$$

in which k is equal to $C_2 V_2 / C_1 V_1$ and C is equal to $C_1 V_1 / V_0$, followed by the concentration of the solution to be determined, which is equal to $3 \times C_0$, because the sample was diluted by 3 in the ascorbic acid.

In order to carry out the iterative calculation, p is given an arbitrary value (close to the theoretical experimental value) in the equation (2). From it is deduced a value of $C_0$, which is reinjected into the equation (1) making it possible to deduce a new value of p, which is in turn reinjected into the equation (2), etc.

The system converges and makes it possible to obtain a final value of $C_0$.

In this way several successive determinations were carried out on the same uranyl nitrate solution. The results obtained are given in the following Table 1.

TABLE 1

| Determination No. | Iodine Concentration |
|---|---|
| 1 | $1.51 \cdot 10^{-7}$ mole/l |
| 2 | $1.55 \cdot 10^{-7}$ mole/l |
| 3 | $1.46 \cdot 10^{-7}$ mole/l |
| 4 | $1.47 \cdot 10^{-7}$ mole/l |
| 5 | $1.67 \cdot 10^{-7}$ mole/l |
| 6 | $1.55 \cdot 10^{-7}$ mole/l |
| 7 | $1.87 \cdot 10^{-7}$ mole/l |

Thus, the mean value is $1.57 \cdot 10^{-7}$ mole/l and the standard deviation $1.40 \cdot 10^{-8}$ mole/l.

The confidence interval calculated for a probability of 95% is $0.13 \cdot 10^{-7}$ mole/l. The repeatability is 8.3% at the 95% probability level.

According to a preferred performance method for the determination according to the invention, the iterative calculation of the iodide ion concentration takes place from the following equation (3):

$$C_0 = C_1[(k+1)/2(\coth\alpha 2 - 1) - (\coth\alpha 1 - 1) \cdot /2]/(1 - ) \qquad (3)$$

assuming
$\alpha 1 = (E_2 - E_1) LN(10)/2p$
$\alpha 2 = (E_3 - E_1) LN(10)/2p$ $$p = \frac{RT}{nF}$$

$= (e^{\alpha 1 - \alpha 2}) - \ch\alpha 2/\ch\alpha 1$
$k = C_2 V_2 / C_1 V_1$

In this calculation, it is assumed, which corresponds to experimental reality, that:
  the solubility of the crystal of the electrode in the solution is the limiting factor regarding the use of the electrode at low concentrations,
  the cationic species associated with the iodides in the crystal of the electrode is absent from the analyzed solutions,
  that the determined addition does not significantly modify either the volume or the ionic strength of the initial solution (in the latter hypothesis, the activity coefficient of the iodide ions remains constant and it is then possible to replace in the particular case of the calculations the activity of the ions by their concentration).

This equation is an explicit expression of the sought concentration $C_0$, as a function of the corresponding additions and potentials.

For very low concentrations, where the addition of a quantity of iodide ions equivalent to the initial quantity supplied by the sample leads to potential jumps below 5 mV, the standard procedure leads to errors of approximately 500%. The procedure described here gives a result whose accuracy can be a few % if the potentials read are sufficiently precise.

FIG. 3 shows the response curves of the electrode used as a function of the iodine concentration of the sample, expressed in logarithmic form in mole/l at 0° C. (curve 1) and 25° C. (curve 2).

The comparison of the two curves shows the gain, in terms of determination thresholds, obtained by choosing a temperature of 0° C.

On referring to the linear part of the response of the electrode, it can be seen that working at 0° C. makes it possible to measure concentrations of approximately $10^{-8}$M, whereas at 25° C. the concentrations measured under similar conditions leads to $3 \cdot 10^{-7}$M. Thus, working at 0° C. leads to a gain by a factor of approximately 50.

Moreover, as a result of being able to determine by iterative calculation the "gradient" of the electrode, it is possible to use the non-linear part of the curve of the selective electrode: millivolts=f(concentration) and therefore bring about sensitivity threshold gains.

In the example given, it is possible to estimate concentrations up to approximately $3 \cdot 10^{-9}$M, which finally leads to a sensitivity gain of 100 compared with the conventional process.

Thus, as a result of the choice of the temperature and the iterative calculation method, the determination process according to the invention leads to a good sensitivity and to a good reproducibility of the results and at the same time lowers the determination threshold.

Measurements of an iodide concentration of approximately $1.5 \cdot 10^{-7}$ mole/l on solutions containing 250 g/l of uranium and having a nitric acidity of 3N, were not disturbed by the presence of the following ions:

$Al^{3+}$: 100 mg/l
$Co^{2+}$: 200 mg/l
$Mg^{2+}$: 30 mg/l
$Mn^{2+}$: 30 mg/l
$Sr^{2+}$: 30 mg/l
$Zn^{2+}$: 30 mg/l

For these determinations, the average durations are 20 min for $10^{-5}$ mole/l iodine solutions and 60 min for low iodine concentrations ($5 \cdot 10^{-8}$M).

Other measurements performed on iodide solutions having an iodide concentration of $10^{-6}$ mole/l and a 3N nitric acidity have lead to the results given in Table 2 for the two calculation methods. For these determinations use was made for the first addition of a concentration $C_1$ and a volume $V_1$, so as to approximately double the concentration in the cell, whilst for the second addition use was made of a volume $V_2$ and a concentration $C_2$, so that $V_2 C_2 = 5 V_1 C_1$.

In the case of the second calculation method (equation (3)), the value of p was 56 mV. This second method more specifically relates to the low concentration range, where the graphic representation is not linear and for which no experimental values are available.

The results obtained on 11 determinations are given in Table 2. The results of Table 2 confirm the accuracy of the determination process.

E) carrying out a second iodide addition to the sample by adding thereto an iodide solution volume $V_2$ containing the same reducing agent and having a known iodide concentration $C_2$, F) measuring the potential difference $E_3$ between the selective electrode and the reference electrode following said second iodide addition to the sample and G) determining from $E_1$, $E_2$, $E_3$, $V_1$, $V_2$, $C_1$ and $C_2$ the iodide concentration $C_0$ of the reduced sample and the iodine concentration of the solution, stages B to F being performed at a temperature of 0° to 5° C.

2. Process according to claim 1, characterized in that the reducing agent is ascorbic acid.

3. Process according to claim 1, characterized in that the selective iodide ion electrode is an AgI/AgS electrode.

4. Process according to claim 1, characterized in that the reference electrode is a mercurous sulphate electrode.

5. Process according to either of the claims 3 and 4, characterized in that the stages B) to F) are performed at a temperature of approximately 0° C.

6. Process according to claim 1, characterized in that the volumes $V_1$ and $V_2$ of the first and second additions are at the most equal to $10^{-3} V_0$.

7. Process according to claim 1, characterized in that $V_1$ and $C_1$ are such that $E_2 - E_1$ is 7 to 15 mV.

8. Process according to claim 1, characterized in that

TABLE 2

|  | $E_1$(mV) | $E_2$(mV) | $E_3$(mV) | $E_1 - E_2$ | $E_1 - E_3$ | Calculation 1 $C_0$(mole/L) | Calculation 2 $C_0$ mole/L $\cdot 10^{-6}$ |
|---|---|---|---|---|---|---|---|
|  | −528.1 | −543.8 | −572.8 | 15.7 | 44.7 | $1.029 \cdot 10^{-6}$ | 0.983 |
|  | −527.0 | −542.8 | −571.5 | 15.8 | 44.5 | $9.98 \cdot 10^{-7}$ | 0.996 |
|  | −529.2 | −545.5 | −574.0 | 16.3 | 44.8 | $9.09 \cdot 10^{-7}$ | 1.19 |
|  | −528.8 | −544.0 | −572.4 | 15.2 | 43.6 | $1.073 \cdot 10^{-6}$ | 0.996 |
|  | −530.8 | −546.0 | −574.5 | 15.2 | 43.7 | $1.082 \cdot 10^{-6}$ | 0.992 |
|  | −529.5 | −545.0 | −573.2 | 15.5 | 43.7 | $1.011 \cdot 10^{-6}$ | 1.17 |
|  | −532.0 | −547.2 | −575.4 | 15.2 | 43.4 | $1.048 \cdot 10^{-6}$ | 1.11 |
|  | −531.8 | −547.2 | −575.6 | 15.4 | 43.8 | $1.042 \cdot 10^{-6}$ | 1.07 |
|  | −531.8 | −547.3 | −575.8 | 15.5 | 44.0 | $1.035 \cdot 10^{-6}$ | 1.05 |
|  | −531.9 | −547.2 | −575.9 | 15.3 | 44.0 | $1.074 \cdot 10^{-6}$ | 0.936 |
| Mean value | −529.8 | −545.4 | −574.0 | 15.6 | 44.2 | $1.022 \cdot 10^{-6}$ | 1.049 |
| Standard deviation | 2.02 | 1.71 | 1.53 | 0.51 | 0.85 | $5.543 \cdot 10^{-8}$ | $8.0 \cdot 10^{-2}$ |
| Var. C. | 0.38 | 0.31 | 0.27 | 3.26 | 1.93 | 5.42 |  |

Confidence interval for an individual result (in %) 12.1

We claim:

1. Process for the determination of iodine in low concentration in an aqueous solution containing an oxidizing nitrate, characterized in that it comprises the following successive stages:

A) adding to a sample of the solution to be determined a reducing agent in order to reduce all the iodine contained therein into iodide and obtain a sample of volume $V_0$ having an iodide concentration $C_0$, B) measuring the potential difference $E_1$ between a selective iodide ion electrode and a reference electrode, both immersed in the sample of volume $V_0$, C) carrying out a first addition of iodide to the sample by adding to it an iodide solution volume $V_1$ containing the same reducing agent and having a known iodide concentration $C_1$, D) measuring the potential difference $E_2$ between the selective electrode and the reference electrode after the first iodide addition to the sample, $V_2$ and $C_2$ are such that $$V_2 C_2 = k V_1 C_1.$$

9. Process according to claim 8, characterized in that k is equal to 5.

10. Process according to claim 1, characterized in that the aqueous solution to be determined is a uranyl nitrate solution.

11. Process according to claim 10, characterized in that the aqueous uranyl nitrate solution contains salts.

12. Process according to any one of the claims 1, 8 and 9, characterized in that the calculation of the concentration $C_0$ of the sample of volume $V_0$ takes place by iteration from the two following equations:

$$p = (E_3 - E_1)/\log|1 + (k+1)C/C_0|$$

$$C_0 = C/|10(E_2 - E_1)/p - 1|$$

in which k is equal to $C_2V_2/C_1V_1$ and C is equal to $C_1V_1/V_0$.

13. Process according to any one of the claims 1, 8 and 9, characterized in that the $C_0$ of the sample of volume $V_0$ is calculated by iteration from the following equations:

$$C_0 = C_1[(k+1)/2(coth\alpha 2 - 1) - (coth\alpha 1 - 1) \cdot /2]/(1- \ )$$

with
$$k = C_2V_2/C_1V_1$$
$$\alpha 1 = (E2 - E1)LN(10)/2p$$
$$\alpha 2 = (E3 - E1)LN(10)/2p$$

$$p = \frac{RT}{nF}$$

$$= (e^{\alpha 1 - \alpha 2}) - ch\alpha 2/ch\alpha 1.$$

* * * * *